United States Patent [19]
Levy et al.

[11] Patent Number: 5,827,900
[45] Date of Patent: Oct. 27, 1998

[54] METHOD AND PHARMACEUTICAL PREPARATIONS FOR REDUCING THE ACTIVITY OF CELLS

[75] Inventors: Joseph Levy; Yoav Sharoni, both of Omer, Israel

[73] Assignee: Makhteshim Agan, Beer-Sheva, Israel

[21] Appl. No.: 532,263

[22] Filed: Sep. 22, 1995

Related U.S. Application Data

[63] Continuation of Ser. No. 158,114, Nov. 24, 1993, abandoned.

[30] Foreign Application Priority Data

Nov. 30, 1992 [IL] Israel .......................................... 103920

[51] Int. Cl.$^6$ .................................................... A61K 31/01
[52] U.S. Cl. ............................................................... 514/762
[58] Field of Search ............................................. 514/762

[56] References Cited

U.S. PATENT DOCUMENTS 5,008,295  4/1991  Nishino et al. ......................... 514/766

FOREIGN PATENT DOCUMENTS 393690  10/1990  European Pat. Off. ................ 514/766

1509587  5/1978  United Kingdom .

OTHER PUBLICATIONS

Cancer Letters, 48(2), 135–142(1989) "Inhibition of Growth—" by C.J. Wang, et al.

Proc. Nat. Sci. Counc. ROC, 13(3), 176–183(1989) "Inhibitory Effects—" by C.J. Wang, et al.

Clinical Chemistry, 37(6), 1056(1991) Abstract "Lyncopene Inhibits—" by Countryman, C., et al.

Free Radical Research Communications, 16(6), 401–8(1992) "Carotene–oxygen radical interactions" by Conn, PF, et al.

Pharmacology 4(6), 334–340(1970), "Action of lycopene in the experimental gastric ulcer", MILANI, C., et al.

Cancer Research, 52(20), 5707–12(1992), "Carotenoids Up–regulate—", Zhang, Li–Xin, et al.

Primary Examiner—Jerome D. Goldberg
Attorney, Agent, or Firm—Michael N. Meller

[57] ABSTRACT

A method of reducing the activity of a cell comprises administering to the cell of a subject in need thereof, directly or systemically, a cell activity-reducing effective amount of lycopene. Pharmaceutical composition are derscribed, for inhibiting the growth of cancer cells, comprising as an active ingredient a cancer cell growth-inhibiting effective amount of lycopene.

6 Claims, 13 Drawing Sheets

METHOD AND PHARMACEUTICAL PREPARATIONS FOR REDUCING THE ACTIVITY OF CELLS

This application is a continuation of application Ser. No. 08/158,114, filed Nov. 24, 1993 now abandoned.

FIELD OF THE INVENTION

The present invention relates to a method of reducing the activity of cells, which utilizes pharmaceutical preparations comprising lycopene. The invention further relates to the inhibition of the growth of cancer cells using lycopene as the anticancer active agent.

BACKGROUND OF THE INVENTION

Carotenoids have been suggested to be active in preventing the occurrence of cancer, and have been shown to be effective in inhibiting the growth of cancer cells. β-carotene has been known for a long time to exhibit anti-cancer properties, both from epidemiological studies and from experiments demonstrating its effect as a free radical scavenger.

Recently [U.S. Pat. No. 5,008,295; Murakoshi et al., *J. Natl. Cancer Inst.*, Vol. 81, No. 21, Nov. 1, 1989] it has been shown that α-carotene is a much more potent inhibitor of cancer cell growth than β-carotene. Other recent studies have compared the anti-cancer activities of various retinoids and carotenoids in vitro [Wang, C-J. and Lin, J-K., *Proc. Natl. Sci. Counc. B. ROC*, Vol. 13, No. 3, (1989), 176–183] and in vivo [C-J. Wang et al., *Cancer Letters*, 48 (1989), 135–142]. These works showed that lycopene has an anti-cancer activity which is comparable—but often less than—that of β-carotene. Lycopene has the formula:

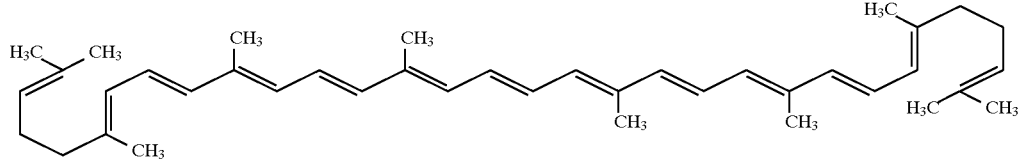

According to the art, lycopene is normally thought not to be active by itself, since the anti-cancer activity of certain carotenoids is often believed to be associated with provitamin A activity [VanEenwyk, J. et al, *Int. J. Cancer*: 48, 34–38 (1991)]. β-carotene is a precursor of Vitamin A, while lycopene is not.

SUMMARY OF THE INVENTION

It has now been most surprisingly found, and this is an object of the invention, that lycopene is active in reducing the overall activity of cells, both in vitro and in vivo.

It has further been found, and this is another object of the invention, that contrary to the teachings of the prior art lycopene can be used as an active agent for the inhibition of growth of cancer cells, and that the concentration of lycopene needed for inhibition is much lower than that needed, e.g., with α-carotene.

It has further been found, and this is another object of the invention, that lycopene can be used effectively to inhibit the growth of certain particularly aggressive cancer cells, which have been only slightly, if at all, inhibited by several conventionally employed anti-cancer drugs.

It has further been found, and this is still another object of the invention, that lycopene can be used effectively to reduce cancer cell count and tumors size.

It is an object of the invention to provide a method for reducing the activity of a cell, which method comprises the use of lycopene as the active ingredient.

It is another object of the invention to provide cancer growth-inhibiting composition, comprising lycopene as an active ingredient.

It is a further object of the invention to provide anti-cancer compositions based on lycopene, which can be relatively well tolerated by a patient in need thereof.

It is still another object of the invention to provide a method of treatment useful for a variety of cancer patients, based on the use of lycopene as the active material.

Other objects and advantages of the invention will become apparent as the description proceeds.

In one aspect, therefore, the invention is directed to a method of reducing the activity of a cell, comprising administering to the cell of a subject in need thereof, directly or systemically, a cell activity-reducing effective amount of lycopene.

According to a preferred embodiment of the invention, the cells the activity of which it is desired to inhibit are cancer cells. Thus, in another aspect, the invention is directed to a method of inhibiting the growth of cancer cells according to the invention, comprises administering to a subject in need thereof a growth-inhibiting effective amount of lycopene. It is notable that the results obtained in the art, when lycopene was tested [Wang et al., ibid], teach away from the present invention by rating the activity of lycopene near or below that of β-carotene. The discouraging results obtained by the previous investigators are probably imputable to specific experimental conditions used by them, although the inventors do not wish to be bound by any particular theory.

DETAILED DESCRIPTION OF THE INVENTION

Figure 1:
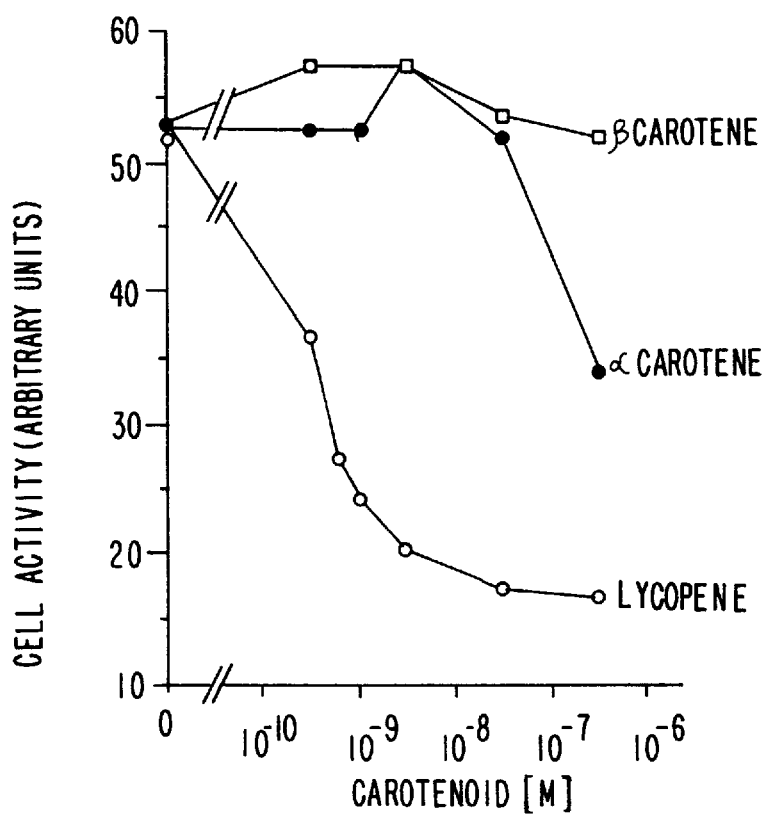
FIG. 1 shows a comparison of inhibition of cell activity by different doses of carotenoids on Ishikawa Endometrial cancer cells.

Lycopene is a naturally occurring material, found in abundance in tomatoes as well as in other fruits and vegetables. It can also be produced synthetically or biosynthetically, e.g., by genetic engineering methods such as those described in EP 393,690. When preparing lycopene from a natural source, e.g., tomatoes, the tomatoes are crushed, concentrated, and the lycopene-containing lipid fraction is extracted therefrom using a suitable solvent, e.g., acetone or an oil, from which it is then separated. Lycopene is substantially water-insoluble and therefore its further purification is relatively simple. As will be apparent to the skilled chemist, extracting lycopene from tomatoes or other natural sources, such as algae, poses no particular technological problems.

Lycopene has been found to be a potent inhibitor of mitochondrial activity. Cell activity is measured by the MTT method, which is based on the activity of mitochondrial dehydrogenases. Surprisingly, the cell activity is not a direct measure of cancer cell growth, and these two values correlate well only at high lycopene concentrations. In other words, cell activity, as measured by the activity of mitochondrial dehydrogenases, is not directly proportional to the reduction of cancer cells growth at low lycopene contents. Thus, in the context of the present invention, reduction of cell activity should be construed in a broader sense than inhibition of cancer cells growth. The exact nature and results of the reduction of cell activity, as measured by the MTT method, has not been fully elucidated. However, part of the mitochondrial activity reduction appears to have a clear inhibiting effect on the growth of cancer cells, as more fully described hereinafter.

According to a preferred embodiment of the invention, lycopene used in method of the invention is a natural extract, particularly a tomato extract.

In another embodiment of the invention the lycopene used is a biosynthetic or a synthetic product.

Depending on the type of disease involved and the area affected, lycopene can be administered in different ways. In localized superficial tumors lycopene can be administered topically or by in situ injection. When systemic activity is required, lycopene can be injected or given orally or by rectal administration. Because of its lipolitic nature, lycopene can be administered topically also when systemic activity is required.

Lycopene, as said, is substantially water-insoluble and, therefore, certain applications require its solubilization, e.g., by fine suspension, use of surface-active agents, by the combination of two or more solubilization means, etc. Other conventional pharmaceutical vehicles and delivery systems, which are well known in the art, can of course be employed and therefore are not discussed herein in detail, for the sake of brevity.

Lycopene can be administered alone, or together with other pharmaceutically-active materials, carriers, adjuvants and additives, and furthermore it can be administered by many different routes. These conventional materials and administration routes can be, for instance—but without limitation—those described in the aforementioned U.S. Pat. No. 5,008,295.

Lycopene has been found to be surprisingly active in inhibiting the growth of a variety of cancer cells, and the invention is not to be construed as being limited to any particular type of cancer cell. Illustrative and non-limitative examples of such cancer cells the growth of which can be inhibited according to the method of the invention are: mammary cancer, endometrial cancer, prostatic cancer, ovarian cancer, lung cancers (small and non-small cell types), melanomas, bladder cancer, pancreatic cancer, gastric cancer, hepatic cancer, leukemias, glioblastoma, neuroblastoma and other brain tumors, and cervical cancer.

The invention is also directed to pharmaceutical compositions for reducing the activity of mammalian cells, particularly—but non limitatively—for inhibiting the growth of cancer cells, which compositions comprise as an active ingredient a cancer cell growth—inhibiting effective amount of lycopene, alone or in combination with pharmaceutically acceptable carriers, adjuvants or additives.

DETAILED DESCRIPTION OF PREFERRED EMBODIMENTS

The invention will now be further illustrated through the following illustrative and non-limitative examples.

General Procedures

Carotenoid sources

Figure 6A:
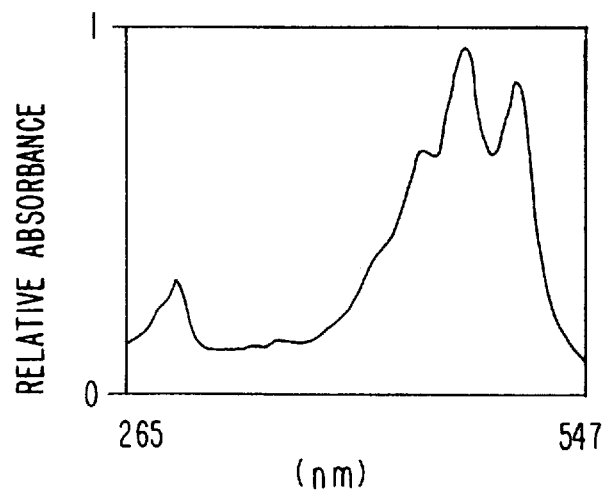
FIG. 6 shows the enlarged absorption spectra of lycopene from two different sources: purified tomato extract, ex Sigma (FIG. 6(*a*)) and freshly prepared tomato extract (FIG. 6(*b*))
Figure 6B:
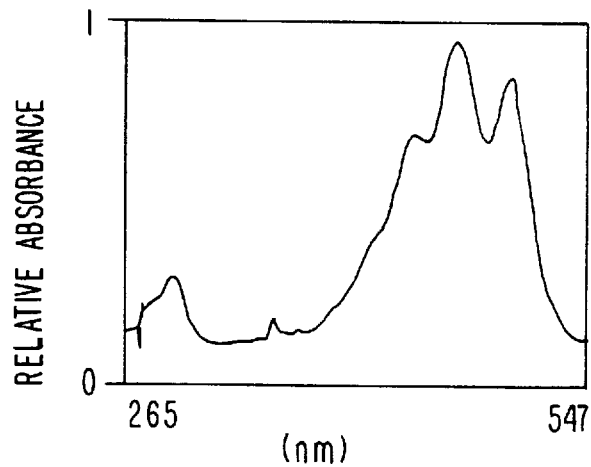

Lycopene was obtained from different sources: 1) commercial material from Sigma 2) an extract specifically prepared for the experiments described below, by extraction from tomatoes, as explained above (5% tomato oleoresin); 3) all-trans synthetic lycopene (Hoffman La-Roche). The commercially available lycopene (ex Sigma), shown in FIG. 6($a$), was spectrophotometrically compared with the extract freshly prepared for the experiments described below (FIG. 6($b$)), and it can be seen that no substantial differences can be found.

α and β carotene were purchased from Sigma.

Cell lines and cultures

HEC-IA human endometrial cell line was obtained from the American Type Culture Collection (Rockville, Md.). It represents a clone originating from endometrial papillary adenocarcinoma of a 71 year old patient and is hormone independent.

The hormone dependent Ishikawa human endometrial cell line originating from a well-differentiated tumor was kindly supplied by H. Rochefort (Institute National de la Sante et de la Recherche Medicale, Montpellier, France).

MCF-7 human mammary cancer cells originating from a well-differentiated tumor was kindly supplied by H. Rochefort (Institute National de la Sante et de la Recherche Medicale, Montpellier, France).

Cell culture

MCF-7 (mammary) Ishikawa and HEC-IA (endometrial) human cancer cells were grown in 75-cm² flasks in Dulbecco modified Eagle's medium (Biological Industries, Beth Haemek, Israel) containing penicillin (100 U/ml), streptomycin (0.1 mg/ml), nystatin (12.5 µg/ml), insulin (0.6 µg/ml), and 10% fetal calf serum.

Cell growth

Cells were stripped of endogenous steroids according to the procedure of Vignon et al. [*Biochem. Biophys. Res. Comm.*, Vol. 146, No. 3, 1987] by successive passages in medium without phenol red containing 10% and then 3% of charcoal-stripped fetal serum (FCS/DCC), by plating into 96-well plates (12,000–20,000 cells per well) in a medium containing 3% FCS/DCC without insulin. One day later the medium was changed to 3% FCS/DCC supplemented with additions as indicated in the figure legends for various periods of time.

Cell activity by the MTT method

After incubation, the mitochondrial activity was estimated by the cellular reduction of MTT to a blue formazan product (Sigma) by mitochondrial dehydrogenases of viable cells. When this product is dissolved in DMSO, its absorbance is measured spectrophotometrically by an ELISA.

Estimation of cell number by thymidine incorporation

Figure 7:
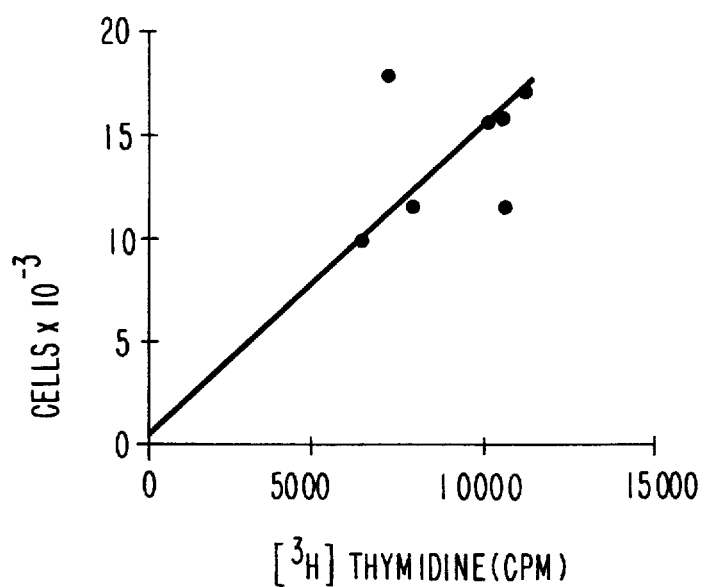
FIG. 7 shows the correlation between thymidine incorporation and cell count in Ishikawa endometrial cancer cells, at different lycopene concentrations.

After incubation, the number of cells and the rate of cell proliferation were estimated by the incorporation of [³H] thymidine into cellular DNA. 10 µC of the labeled thymidine were added to each well and the incubation continued for additional four hours. To stop incorporation, the medium was removed, the wells were washed once with PBS and the cells were detached with 50 µl of trypsin (0.25%), harvested by vacuum filtration on a glassfiber filter and counted in a scintillation counter. To validate the method and correlate the counted radioactivity with number of cells, parallel wells were counted by haemocitometer. A good correlation exist between the two methods (FIG. 7).

Carotenoids solubilization

Carotenoids were applied to the cells by two different methods: 1) as a solubilized material (see below) and as a solution in tetrahydrofuran (THF). No significant effect on cell growth is evident employing 0.1% or 0.5% THF final dilution which is ample for the dissolving maximal concentration of carotenoids needed in the experiments.

Carotenoids were dissolved in THF containing 0.05% BHT as an antioxidant at a maximal concentration of 2 mM. These solutions were used in the day of the experiments or stored at −70° C. for future use. This solution was diluted with THF and added into the medium which was stirred vigorously. The final THF concentration was 0.5%. To verify the final carotenoid concentration, the incubation medium was extracted with isopropanol and with a mixture of hexane/dichloromethane (5:1) and the absorbence was measured by spectrophotometer. All procedures were done in a dim light.

2) The carotenoids were solubilized by mixing them with surface active agents. A typical preparation for lycopene involves adding to one part of a 5% lycopene tomato extract 1 part of Tween 40 (sorbitan monopalmitate, Atlas Corp., U.S.A.), and 1 part of Croduret 50-S (hydrogenated castor oil, ex Croda Chem Ltd., England), mixing under heating, adding to the resulting solution, after cooling, a solution of ascorbic acid in double-distilled water, and filtering if necessary. Corresponding preparations were applied to α- and β-carotenes.

The results presented in FIG. 1–5 are representative. Similar results were obtained in all cell lines, except when stated otherwise.

EXAMPLE 1

Ishikawa Endometrial Cancer Cell Activity

The dose-dependent effect of lycopene, α-carotene (ex Sigma Chemical Co.) and β-carotene (ex Sigma) on cell activity was tested on Ishikawa cell growth. Cells were grown for three days in the presence of the carotenoids at the indicated concentrations. Cell activity was measured as described. The results are the mean of three different experiments, each done in ten replicates.

The results of this experiment are shown in FIG. 1. The $ED_{50}$ for the inhibition of cell activity by lycopene is $\sim 3 \times 10^{-10}$M, (reduction in cell activity from $53 \times 10^3$ to $33 \times 10^3$) compared to $\sim 3 \times 10^{-7}$M for α-carotene. β-carotene, on the other hand, shows no effect in this cell line (the effect shown is not statistically significant).

EXAMPLE 2

Effect of Carotenoids of Different Origin on the Activity of MCF-7 Cancer Line

Figure 2:
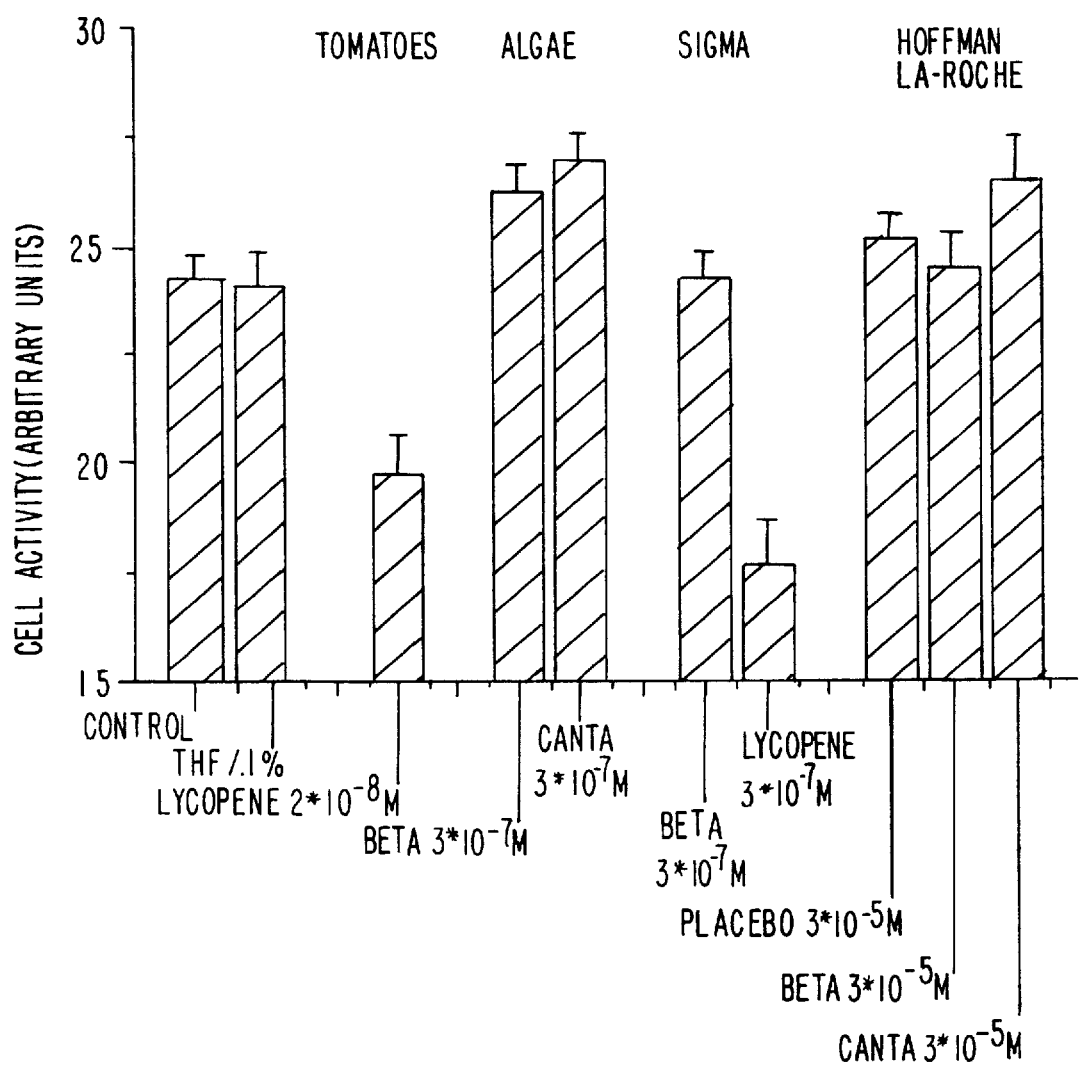
FIG. 2 compares the inhibiting activities of some carotenoids obtained from different sources on MCF-7 mammary tumor cells growth.

The effect of lycopene from different sources was compared with that of other carotenoids, in MCF-7 cancer cells. Cells were grown for three days in the presence of the carotenoids at the indicated concentrations. The results are shown in FIG. 2, where "Tomatoes" identifies solubilized lycopene extracted from tomatoes, dissolved in THF and brought to a content of $2 \times 10^{-8}$M lycopene. Control (no addition) and a 0.1 wt % water solution of THF were also tested.

"Algae" identifies material extracted from algae and obtained from The Institutes for Applied Research of the Ben-Gurion University of the Negev, Beer-Sheva, Israel, where "beta" identifies β-carotene and "canta" identifies canthaxantine, supplied to the cells after initial solubilization in THF.

"Sigma" identifies material purchased from Sigma Chemical Co., St. Louis, Mo., USA., where "beta" identifies β-carotene, supplied to the cells as described above.

"Hoffman La-Roche" identifies material obtained from Hoffman La-Roche, Inc. Nutely, N.J., U.S.A., as water miscible beadlets, where "beta" identifies β-carotene and "canta" identifies canthaxantine.

It is easily seen from FIG. 2 that lycopene, no matter of what origin, was substantially more effective in reducing cell activity.

EXAMPLE 3

Effect on the Activity of HEC-IA Endometrial Cell Line

The time course of the effect of lycopene, α-carotene and β-carotene ($3 \times 10^{-7}$M) on the cell activity of HEC-IA endometrial cancer cells was tested. Cells were incubated for two days with the indicated carotenoids in 96-well plates. The activity of the cells was evaluated by the MTT method.

Figure 3A:
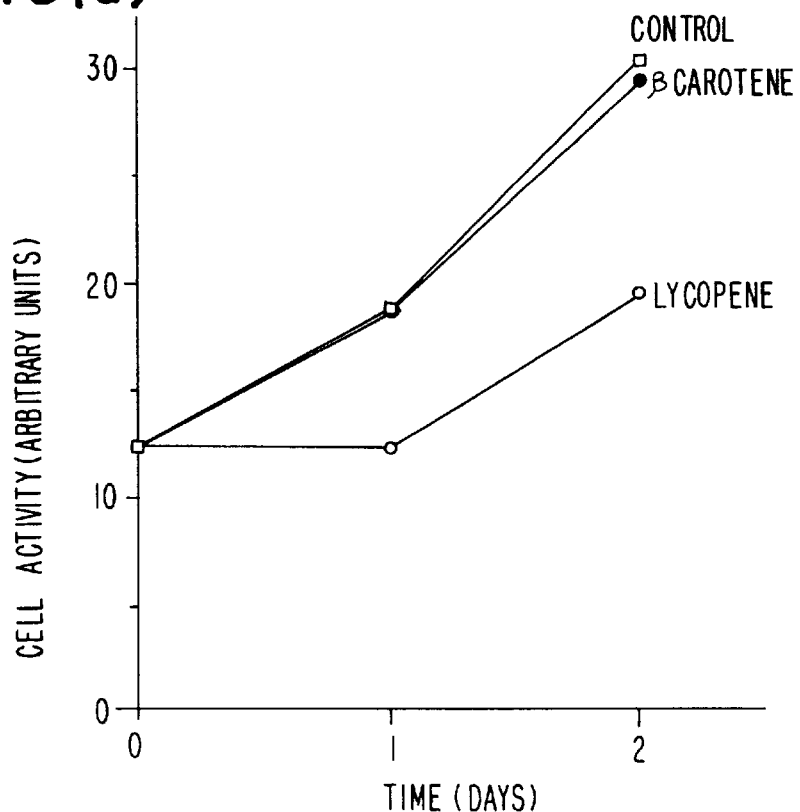
FIG. 3 is a comparison of the inhibiting activity of different carotenoids dissolved originally in either THF or in aqueous solution, on HEC-IA Endometrial cancer cell growth.
Figure 3B:
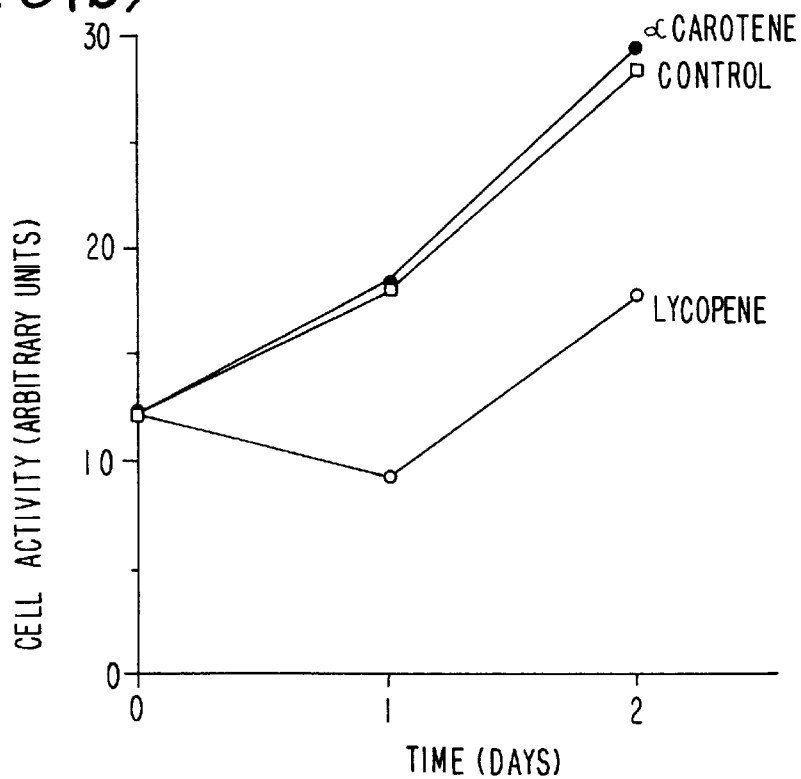

The effects of α-carotene, β-carotene, and lycopene of two origins (Sigma and fresh tomato extract), and of two solutions obtained by two different preparation methods (0.1% THF and water solubilized) were compared. The results are shown in FIG. 3. FIG. 3(*a*) compares the effect of β-carotene with a solubilized lycopene originating from tomato extract, in water solution prepared as described above. The dramatic effect of lycopene in reducing cell activity is self evident, while β-carotene is substantially inactive, its behavior being essentially the same as that of the control. FIG. 3(b) compares the activity of α-carotene and lycopene (the lycopene originating from Sigma and solubilized in 0.1% THF). The same result as in FIG. 3(a) is obtained, where α-carotene also behaves essentially as the control.

EXAMPLE 4

Figure 4:
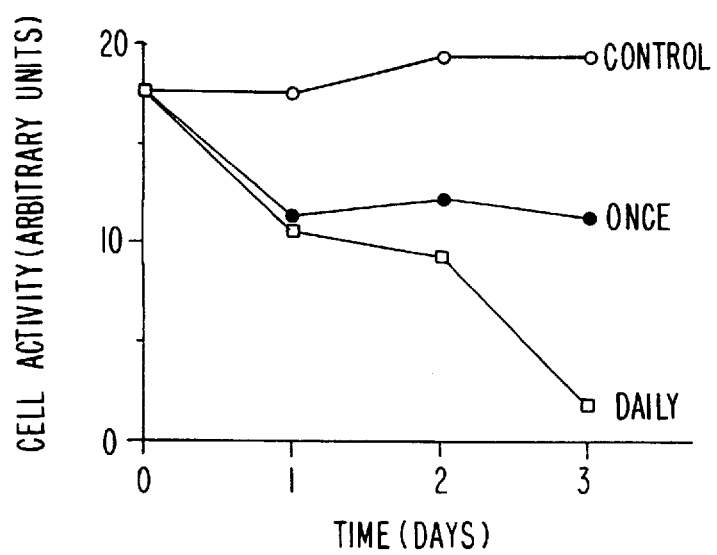
FIG. 4 shows the improved inhibitory effect of a daily application of lycopene, over a single application, on the growth of MCF-7 mammary tumor cells.

Effect of Repeated Daily (Multiple) Applications Versus Single Application of Lycopene on the Activity of MCF-7 Mammary Tumor Cells Lycopene $3\times10^{-7}$M was applied daily (on day 0,1, and 2), or once (on day 0 only). The control contained 0.1% THF. Results are shown in FIG. 4. The medium was replaced daily.

The results suggest that a daily application dramatically improves the activity reducing effect of lycopene on MCF-7 cells. This is probably due to a short, half life of the carotene in the incubation medium. This conclusion is supported by the fact that lycopene does not appear to be effective any more in day 2 when added only once (the control and experimental line being parallel).

EXAMPLE 5

Effect of Lycopene on the Activity of IGF-I-Induced MCF-7 Cells

Figure 5:
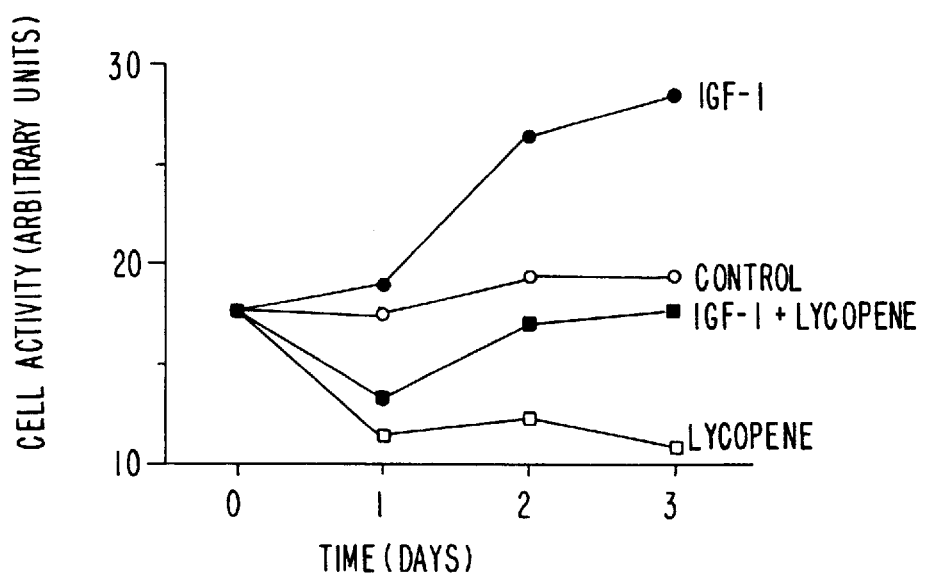
FIG. 5 illustrates the inhibition of IGF-I induced growth of human MCF-7 mammary cancer cells by lycopene.

To answer the question of whether Insulin-like growth factor-I (IGF-I)-induced proliferation was affected by lycopene, the MCF-7 cells were incubated with IGF ($3\times10^{-8}$M). Lycopene reduced the mitochondrial activity of the tumor cells in the absence of IGF-I as well as in those stimulated by IGF-I. In FIG. 5 the activity in the presence of $3\times10^{-7}$ lycopene is lower than with IGF-I alone.

In the following examples in vitro and in vivo inhibition of cancer cell growth is demonstrated. The overall cell activity reduction is not examined and only the inhibiting effect directly pertinent to cancer cell growth is tested.

EXAMPLE 6

Inhibition of Ishikawa Endometrial Cancer Cells Growth

Figure 8:
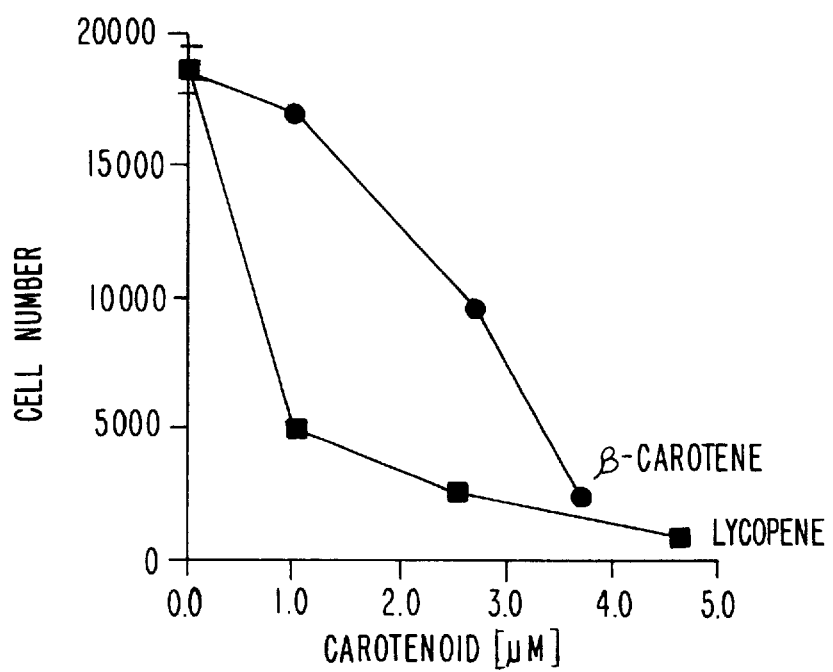
FIG. 8 illustrates the effect of solubilized carotenoids on growth of Ishikawa Endometrial Cancer cells.

The results of this experiment are shown in FIG. 8. From these results it is seen that lycopene requires only 0.8 μM, as compared to 3 μM of β-carotene, to reach a 50% reduction in cell number from $18\times10^3$ to $9\times10^3$.

EXAMPLE 7

Inhibition of H226 Lung Cancer Cells Growth

Figure 9:
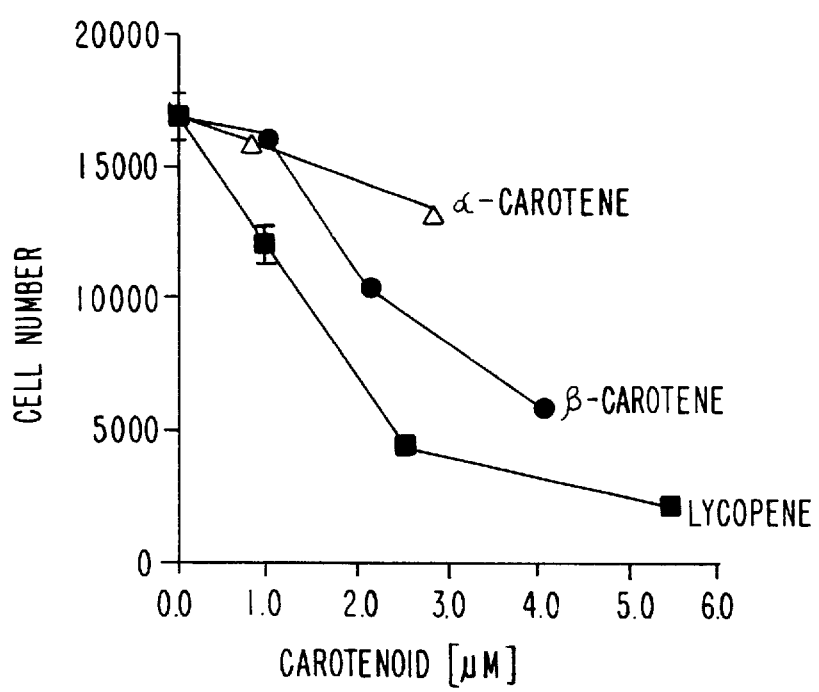
FIG. 9 illustrates the effect of solubilized carotenoids on the growth of H226 lung cancer cells.

The results of this experiment are shown in FIG. 9. From these results it is seen that lycopene requires only 1.8 μM, as compared to 3.5 μM of β-carotene, to reach a 50% reduction in cell number from $17\times10^3$ to $8.5\times10^3$. Higher concentrations of α-carotene are needed for such effects.

Figure 10:
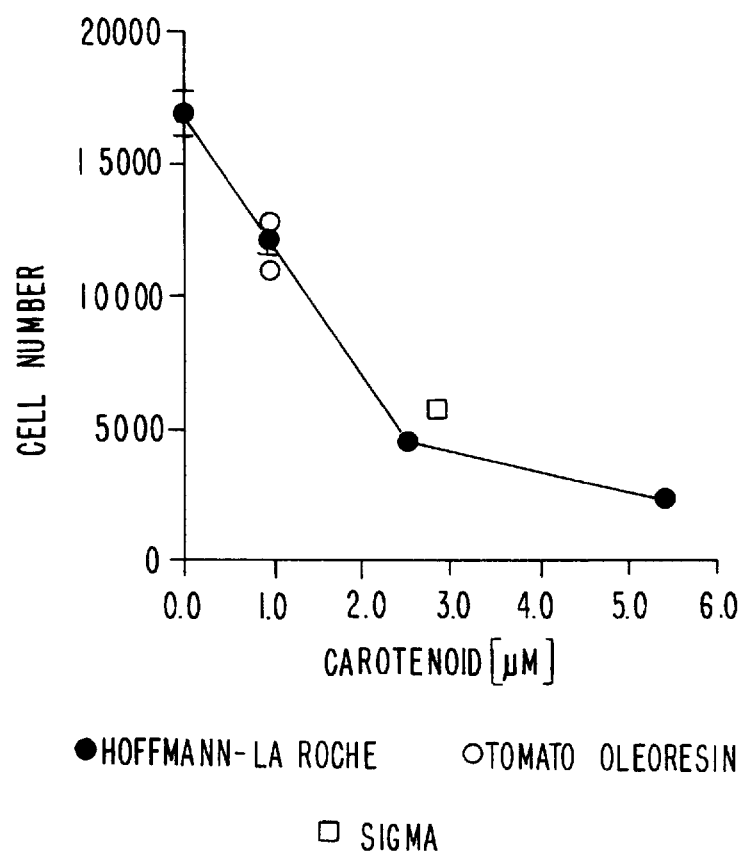
FIG. 10 illustrates the effect of solubilized lycopene from different sources on the growth of H226 lung cancer cells.

These results were confirmed with different preparations of lycopene (FIG. 10), including those obtained from Sigma, Hoffman-La Roche and from tomato oleoresin. It is thus seen that the exact origin of the lycopene employed is not essential.

EXAMPLE 8

Effect of Carotenoids on Induction and Growth of DMBA Induced Rat Mammary Tumors In Vivo The aim of these experiments was to study the effect of lycopene on the number and on the size of DMBA induced rat mammary tumors and to compare it to those of β-carotene.

The rat mammary tumor is an excellent model for hormone dependent human breast cancer, as the tumor growth rate is easily manipulated by estrogens and other hormones [Levy, J. et al, Eur. J. Cancer. Clin. Oncol., 17: 1023–1026, (1981); Sharoni, Y. et al., FEBS Lett., 189: 133–136, (1985); Johnson, M. L. et al., Cancer Res., 43: 2199–2209, (1983)].

Eight to fifteen rats were in each of the following four experimental groups:
 a. control, without any treatment.
 b. placebo, injected i.p. with the vehicle used for solubilization of carotenoids.
 c. lycopene, injected i.p. with solubilized 5% lycopene oleoresin.
 d. β-carotene, injected i.p. with a synthetic material produced by Hoffmann-La Roche.

This experiment was repeated 3 times.

The placebo and the two carotenoids (water solubilized) were administered i.p. twice per week (10 mg/kg). The treatment was initiated two weeks prior to the DMBA tumor induction and continued for twenty weeks. The normal rat diet consist of 50% corn and 50% synthetic ingredients. This diet provides a very low content of carotenoids.

Mammary tumors were induced in rats by 20 mg DMBA (7,12-Dimethylbenz[a]anthracene), as described previously [Sharoni, Y.et al., Eur. J. Cancer Clin. Oncol., 20: 277–281, (1984)]. The rats were inspected twice per week, and tumor size was determined by measurement with a caliper once a week, of diameters in two dimensions perpendicular to each other. The two diameters produced the tumor area. Twenty weeks after beginning of carotenoids administration, all animals were sacrificed and the tumors were removed and kept frozen (−70° C.). Blood was collected, plasma separated and kept frozen under nitrogen for the measurement of carotenoids levels. Pathological analysis of animals did not reveal any tissue damage by either the placebo or carotenoids treatment.

In order to evaluate tie efficiency of carotenoids administration, their levels in blood was measured in separate groups of rats that were treated with carotenoids as described above. Rats were sacrificed every two weeks, 48 hours after the last injection and the blood stored for HPLC analysis. This analysis measures the levels of different carotenoids and their isomers [Elinder, L. S. and Walldius, G., Journal of Lipid Research, 33: 131–137, (1992); Stahl, W. et al., Archives Biochem. Biophys., 294: 173–177, (1992)].

Plasma carotenoids levels.

Figure 11:
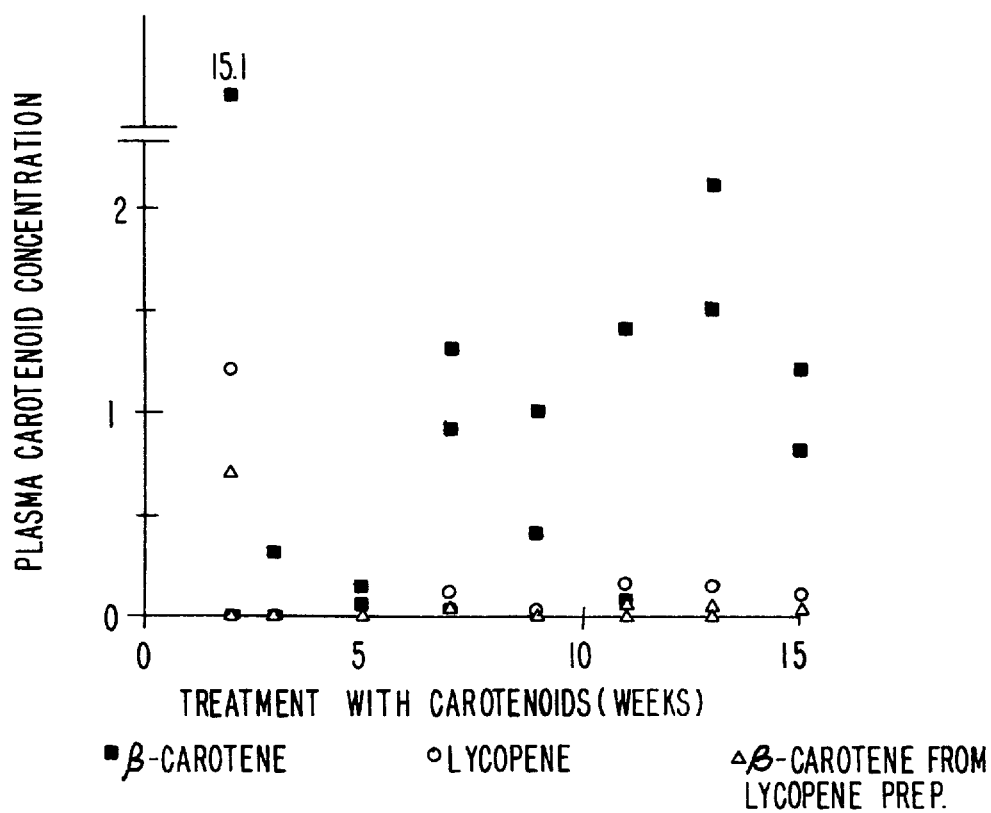
FIG. 11 shows the plasma carotenoids level in rats injected twice weekly with 10 mg/kg β-carotene or lycopene containing ~20% β-carotene.

Lycopene and β-carotene were not detected in the plasma of the control and the placebo treated rats. Carotenoids were detected in the lycopene and β-carotene treated groups (FIG. 11). The level of β-carotene was significantly higher than the level of lycopene although the rats were injected with equal amounts of the two carotenoids. An unidentified peak was detected in plasma of lycopene treated animals. This may represent an oxidized form of lycopene.

Figure 12:
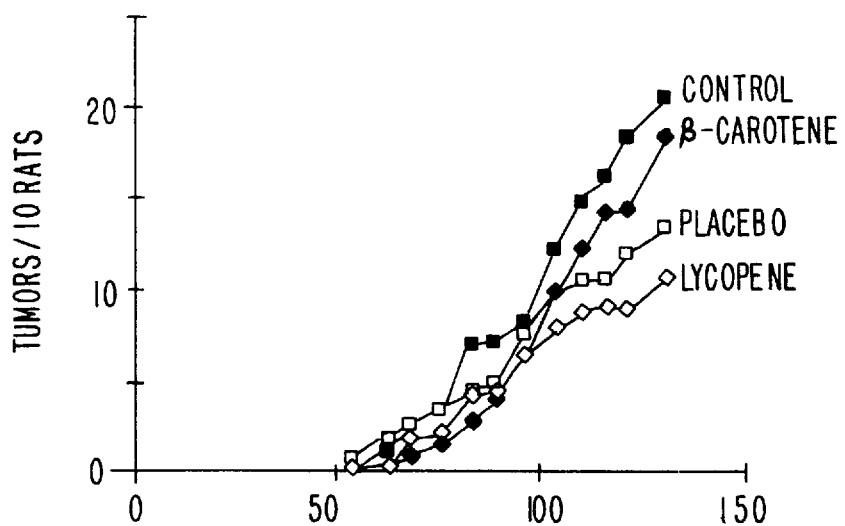
FIG. 12 illustrates the cumulative number of tumors/10 rats in the in vivo experiment of Example 8.
Figure 13:
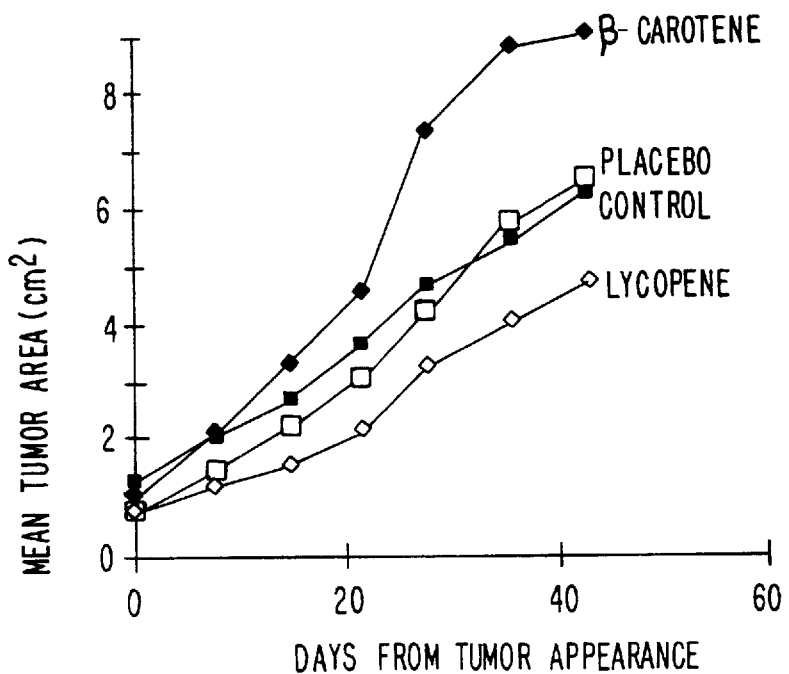
FIG. 13 shows the reduction of the average tumor area of DMBA-induced rat mammary tumors obtained with lycopene in the in vivo experiment of Example 8.

Tumor number and size,

The number of tumors per 10 rat was the lowest in the lycopene treated group (FIG. 12). This result was reproducible in the three experiments. The average tumor size was smaller in the lycopene treated group during most of the experiment (FIG. 13).

EXAMPLE 9

Survival in Nude Mice

Survival experiments were carried out in nude mice (female, c. rivers, 25g, d. fix) implanted i.p. with Ovcar-3 human ovarian carcinoma tumors.

Figure 14:
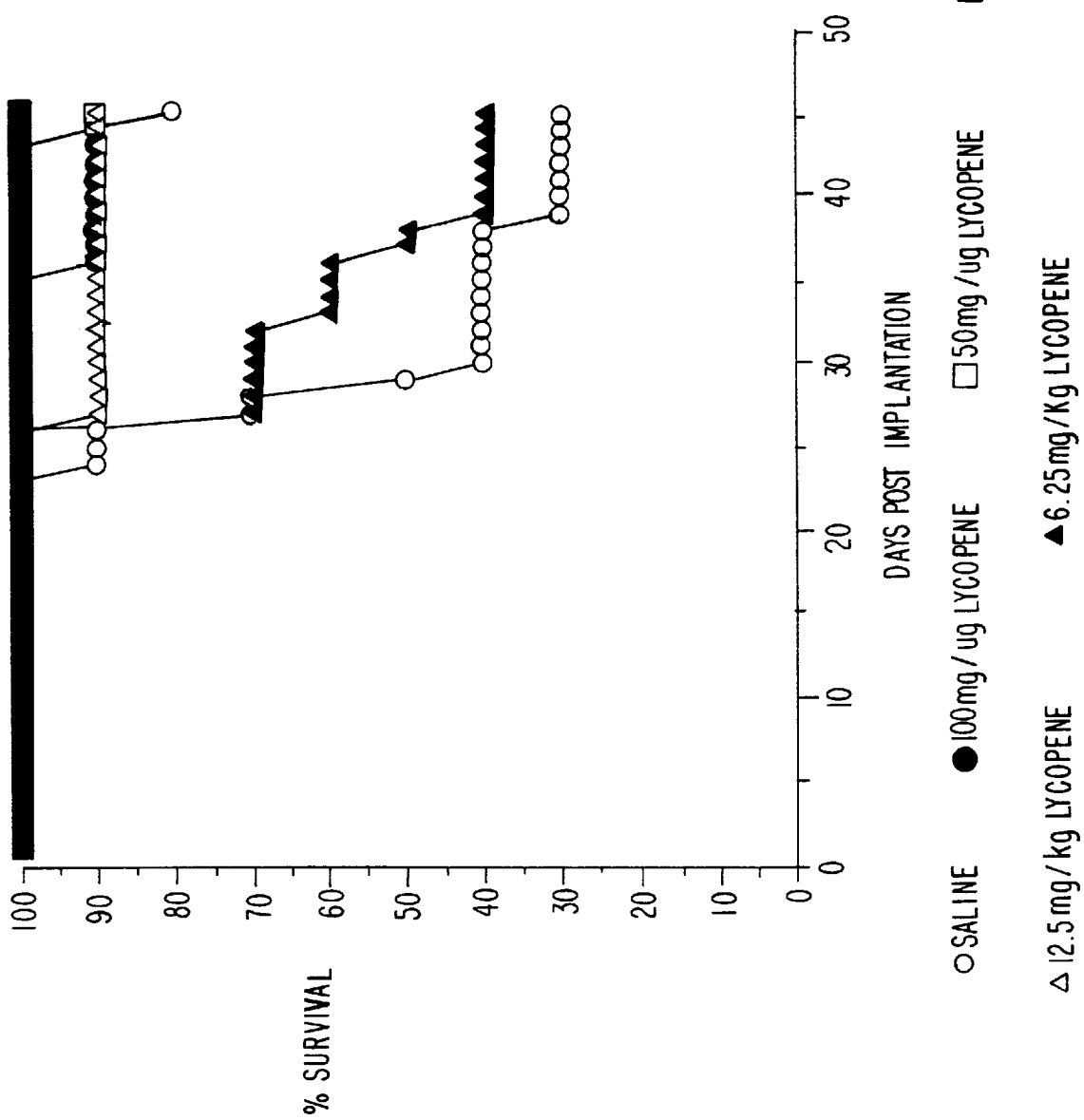
FIG. 14 shows the results of survival experiments in nude mice.

A 5% lycopene suspension (ex Makhteshim) was diluted (1.2 g of lycopene in vial with sterile glass beads) with emulphor/saline, to give 1:10 (w/v) dilution. 60 Nude mice were used in the experiment, in 6 groups of 10 mice each. Tumors were implanted at Day 0, and lycopene was injected daily i.p. during Days 1–10. The groups were treated as follows:

Group 1 (control): Emulphor
Group 2: 100 mg/Kg lycopene
Group 3: 50 mg/Kg lycopene
Group 4: 25 mg/Kg lycopene
Group 5: 12.5 mg/Kg lycopene
Group 6: 6.25 mg/Kg lycopene The mice were examined daily for survival. The results are shown in FIG. 14, which illustrates the effect up to 50 days post-implantation. Significant tumor suppression activity was found in this experiment, down to 12.5 mg/Kg dose.

As will be appreciated by the skilled person, the dose of lycopene that should be used in each case varies depending on the type of tumor, the administration route and the severity of symptoms. Illustrative lycopene dosages are, e.g., 7 mg/Kg to 200 mg/Kg. However, as will be understood, lycopene does not suffer from the severe toxicity problems associated with many cancer drugs and, therefore, relatively high dosages of lycopene can be given to the patient.

Additionally, because of its effect on cell activity, lycopene can also be conveniently administered as a component in anticancer pharmaceutical preparations which contain other and/or conventional anticancer or other pharmaceutical agents, as well as in admixture with other carotenoids and pharmaceutically effective additives.

Lycopene can be administered by different routes, e.g., by intravenous, subcutaneous or intramuscular injection, topically or orally, or rectally by suppository.

Pharmaceutical preparations according to the invention, containing a therapeutically-effective amount of lycopene, can be prepared in combination with pharmaceutically-acceptable carriers, by known methods. Examples of acceptable carrier and adjuvants are: surface active agents, e.g., sucrose fatty acid ester, propyleneglycol fatty acid ester, lecithin, etc.; sucrose, lactose, starch, manitol, calcium carbonate, sodium bicarbonate and other useful vehicles; binders, e.g. gum arabic, gelatin, etc.; lubricants, such as talc or magnesium stearate; flavors and preserving agents; oils, such as coconut oil, olive oil, soybean oil; fillers, coatings, emulsifiers and the like conventional additives.

Preparations can be made for oral administration, e.g., in the form of soft and hard capsules, tablets, granules, grains, powder, and they can be in slow-release form, or they may be in liquid form, e.g., as suspensions. For parenteral administration other commonly employed forms, such as injections, drops, suppositories, etc., can be used. Illustrative examples of preparation are:

Preparation A

10 G. of lycopene is suspended in 1 Kg of soybean oil. The suspension is filled in gelatibe capsules (about 1000 capsules).

Preparation B

12 G of lycopene are diluted with emulphor/saline, to give 1:10 (w/v) dilution. The resulting solution is used as an injectable solution.

Preparation C

1 G of lycopene is mixed with gerntle warming with 3 Kg of a mixture including 1.7 Kg of hydrogenated jojoba wax and 13 Kg of glycerol monostearate in liquid jojoba wax. An ointment is obtained which is suitable for topical application.

The invention has been described with reference to illustrative and non-limitative examples. Many changes can be made in the materials and methods discussed. For instance, different solubilization methods, vehicles and delivery systems can be employed, other concentrations can be used and other types of cells can be treated, all without exceeding the scope of the invention.

We claim:

1. A method of inhibiting the growth of cancer cells sensitive to lycopene, wherein the cancer cells the growth of which is to be inhibited are selected from the group consisting essentially of mammary cancer, endometrial cancer, ovarian cancer, and lung cancer comprising administering to a subject in need thereof a composition consisting essentially of lycopene, said composition containing a growth-inhibiting effective amount of lycopene wherein the lycopene is natural extract, a biosynthetic product or a synthetic product.

2. A method according to claim 1 wherein said composition which consists essentially of lycopene is administered by injection or orally.

3. A method according to claim 1, wherein lycopene is administered topically, by injection or orally.

4. A method of treating a cancer patient having a mammary cancer, endometrial cancer, ovarian cancer or lung cancer, said cancer cells being sensitive to lycopene, comprising administering to said patient a pharmaceutically-effective amount of lycopene, said lycopene being in the form of a composition consisting essentially of lycopene in a cancer cell growth inhibiting effective amount as the active ingredient for inhibiting the growth of cancer cells, and wherein said composition consists essentially of lycopene in a pharmaceutically acceptable carrier.

5. A method of treating one or more tumors in a patient having mammary cancer, endometrial cancer, ovarian cancer or lung cancer, said cancer cells being sensitive to lycopene, comprising administering to said patient a tumor growth-inhibiting effective amount of lycopene in a pharmaceutical composition consisting essentially of lycopene as the active ingredient for inhibiting the growth of one or more tumors, and wherein said composition, consists essentially of lycopene in a pharmaceutically acceptable carrier.

6. A method of using a lycopene composition for inhibiting the growth of cancer cells selected from the group consisting of mammary cancer, endometrial cancer, ovarian cancer, and lung cancer, by administering an anti-cancer cell effective amount of said composition consisting essentially of lycopene to the cancer cell, wherein said lycopene composition is in the form of a topical preparation, in injectable form, or as an orally administrable formulation.

* * * * *